United States Patent
Wei et al.

(10) Patent No.: US 10,969,357 B2
(45) Date of Patent: Apr. 6, 2021

(54) METHOD OF ENHANCING JUDGMENT OF GAS DETECTOR

(71) Applicant: Jing-Cheng Wei, Minxiong Township, Chiayi County (TW)

(72) Inventors: Jing-Cheng Wei, Minxiong Township (TW); Jun-Ting Wei, Minxiong Township (TW)

(73) Assignee: Jing-Cheng Wei, Minxiong Township (TW)

( * ) Notice: Subject to any disclaimer, the term of this patent is extended or adjusted under 35 U.S.C. 154(b) by 0 days.

(21) Appl. No.: 16/383,819

(22) Filed: Apr. 15, 2019

(65) Prior Publication Data
US 2020/0326294 A1    Oct. 15, 2020

(51) Int. Cl.
*G01N 27/04* (2006.01)
*G08B 21/12* (2006.01)
*G01N 33/00* (2006.01)

(52) U.S. Cl.
CPC ....... *G01N 27/046* (2013.01); *G01N 33/0063* (2013.01); *G08B 21/12* (2013.01)

(58) Field of Classification Search
None
See application file for complete search history.

(56) References Cited

U.S. PATENT DOCUMENTS

| 4,351,181 A * | 9/1982 | Currans | G01N 33/0062 340/634 |
| 2004/0113802 A1* | 6/2004 | Green | G01N 27/16 340/632 |
| 2007/0192041 A1* | 8/2007 | Goldstein | G01N 21/27 702/24 |
| 2008/0182215 A1* | 7/2008 | Sid | G01N 33/0063 431/18 |
| 2010/0085199 A1* | 4/2010 | Gonzales | G08B 29/043 340/629 |
| 2010/0294021 A1* | 11/2010 | Makino | G01N 25/18 73/25.03 |
| 2011/0018726 A1* | 1/2011 | Gonzales | G08B 29/185 340/628 |
| 2011/0049342 A1* | 3/2011 | Tsao | G01N 21/274 250/252.1 |

(Continued)

*Primary Examiner* — Steven Lim
*Assistant Examiner* — Muhammad Adnan
(74) *Attorney, Agent, or Firm* — Alan D. Kamrath; Karin L. Williams; Mayer & Williams PC

(57) ABSTRACT

A method of enhancing judgment of a gas detector contains: dividing a voltage difference between an output signal voltage and an environmental detection voltage of the gas detector into several parts. Each of multiple detecting processes of the gas detector is captured by a microprocessor at the environmental detection voltage for ten times in each microsecond, and a predetermined detection time of each detecting process is 10 seconds. When the environmental detection voltage changes linearly, the predetermined detection time of each detecting process is shorten to 1/10 second/per time. After three successive detection processes change linearly, a warning device is started. Otherwise, the microprocessor compensates the output signal voltage and recovers the predetermined detection time when the environmental detection voltage changes so as to maintain the voltage difference at a certain value.

2 Claims, 2 Drawing Sheets

(56) References Cited

U.S. PATENT DOCUMENTS

| | | | |
|---|---|---|---|
| 2012/0078532 A1* | 3/2012 | Forsyth | G01N 21/274 702/24 |
| 2012/0126975 A1* | 5/2012 | Gonzales | G08B 29/26 340/540 |
| 2014/0053631 A1* | 2/2014 | Watanabe | G01N 9/36 73/30.01 |
| 2014/0375463 A1* | 12/2014 | Duric | G01N 27/4163 340/632 |
| 2016/0061756 A1* | 3/2016 | Yamashita | G01N 33/005 73/25.03 |
| 2020/0064331 A1* | 2/2020 | Yamada | G01N 33/4972 |

* cited by examiner

METHOD OF ENHANCING JUDGMENT OF GAS DETECTOR

BACKGROUND OF THE INVENTION

Field of the Invention

The present invention relates to a method of enhancing judgment of a gas detector which compensates an output signal voltage and recovers a predetermined detection time when temperature and humidity change, thus enhancing the detection of harmful gas.

Description of the Prior Art

As far as the sense of smell is concerned, human beings are unable to distinguish gases. Among colorless and odorless gases, there are some gases that are harmful (such as carbon monoxide) to the human body. When human beings breathe excessive harmful gases, the gases may cause coma and death. To avoid such a danger, a gas detector is applicable for a detection of harmful gases. Furthermore, carbon dioxide and oxygen are closely related to the quality of human life. For instance, air-conditioning systems may use gas detectors to detect carbon dioxide and oxygen concentrations or to detect pollutant concentrations, so as to adjust gas concentration or to start an air purifier based on a gas standard, and so a gas detector is important for improving the comfort of human life.

A harmful gas detector converts a specific harmful gas (i.e., a gas to be tested), contained in a gas "generally referred to as undetected air", into an element that can be monitored or measured with an appropriate electrical signal (voltage, current, resistance). It is like the smell ability of animals, commonly known as "electronic nose" so as to detect the harmful gases and to send an output signal voltage (the higher the concentration of harmful gases, the lower the resistance of the harmful gas detector and the higher the voltage), and trigger a warning device (such as a flashing light or a buzzer) to generate an alerts. However, the gas detector makes a comparison based on a curve diagram in which a relationship between a voltage and a concentration of the harmful gases is shown in FIG. 1 so as to detect the harmful gases and to send a voltage signal, thus having a long response time and unsatisfactory safety.

A conventional method of detecting the harmful gases by using a gas detector is inefficient, and it is not always necessary for general household users to detect the type of harmful gas detected. After all, it is necessary to raise the alert and eliminate it when the harmful gas is found. It is important to provide extra time for safe disposal of the harmful gas. As for wasting time to determine what kind of harmful gas is detected, it is completely useless for general users (and specific harmful gases must be added with odorants according to regulations so as to alert people to the detection of specific harmful gases).

The present invention has arisen to mitigate and/or obviate the afore-described disadvantages.

SUMMARY OF THE INVENTION

The primary objective of the present invention is to provide a method of enhancing judgment of a gas detector which compensates an output signal voltage and recovers a predetermined detection time when temperature and humidity change, thus enhancing the detection of harmful gas.

A method of enhancing judgment of a gas detector provided by the present invention includes: dividing a voltage difference between an output signal voltage and an environmental detection voltage of the gas detector into several parts, wherein each of multiple detecting processes of the gas detector is captured by a microprocessor at the environmental detection voltage for ten times in each microsecond, and a predetermined detection time of each detecting process is 10 seconds, wherein when a change of the environmental detection voltage changes linearly, the predetermined detection time of each detecting process is shorten to $1/10$ second/per time. After three successive detection processes change linearly and a relationship between a time of the environmental detection voltage and a voltage changes linearly, a warning device is started (wherein the gas detector is configured to detect harmful gas). Otherwise, the gas detector judges a natural change in an environment when a temperature and humidity change (i.e., a non-linear change), in the meantime, the microprocessor compensates the output signal voltage and recovers the predetermined detection time when the environmental detection voltage changes so as to maintain the voltage difference at a certain value (for example, the environmental detection voltage is less than 0.5 volts of the output signal voltage, wherein when the microprocessor acquires that the environmental detection voltage produces a 0.1 volt change with a change of the temperature and humidity, the microprocessor requires the output signal voltage to produce the 0.1 volt change so that the environmental detection voltage is less than 0.5 volts of the output signal voltage so as to avoid an error report because the environmental detection voltage is increased based upon the temperature and humidity change).

DETAILED DESCRIPTION OF THE PREFERRED EMBODIMENTS

The present invention will be clearer from the following description when viewed together with the accompanying drawings, which show, for purpose of illustrations only, a preferred embodiment in accordance with the present invention.

Figure 1:
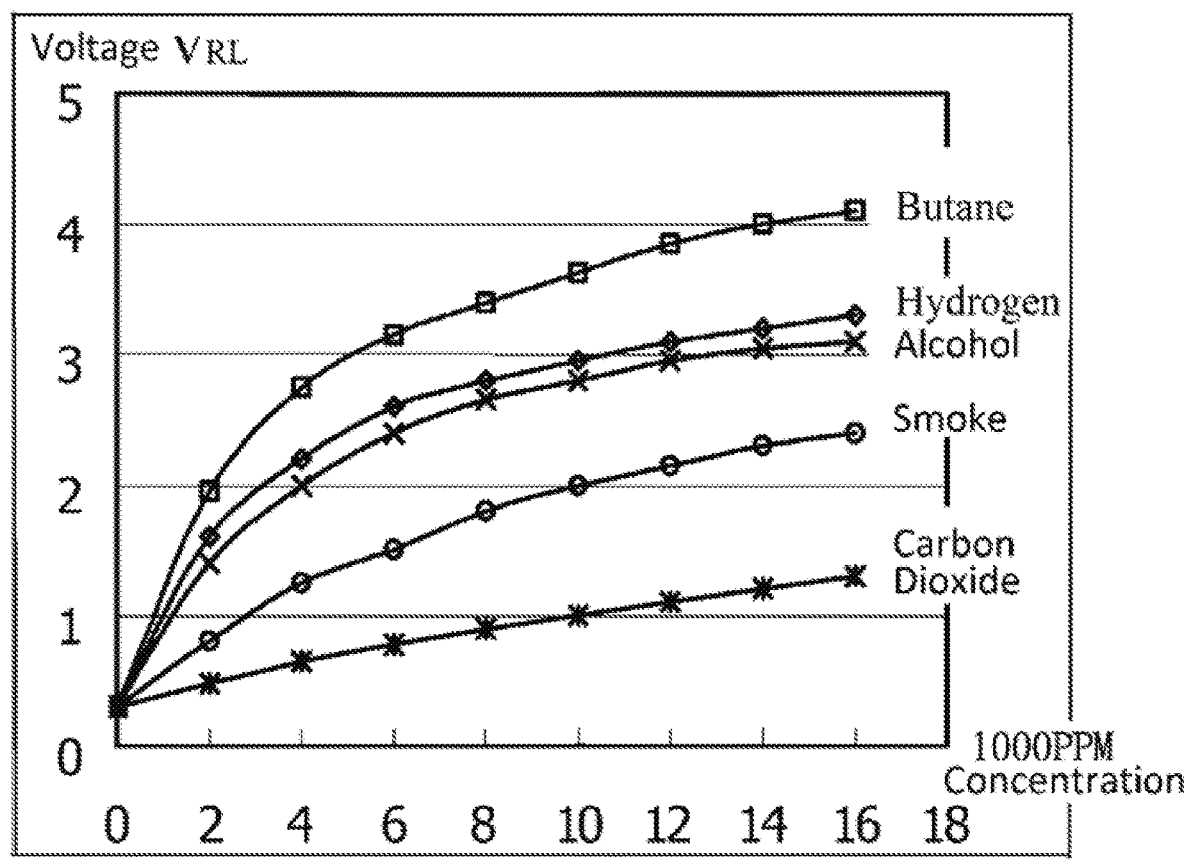
FIG. 1 is a curve diagram of a conventional relationship between a voltage and a concentration.
Figure 2:
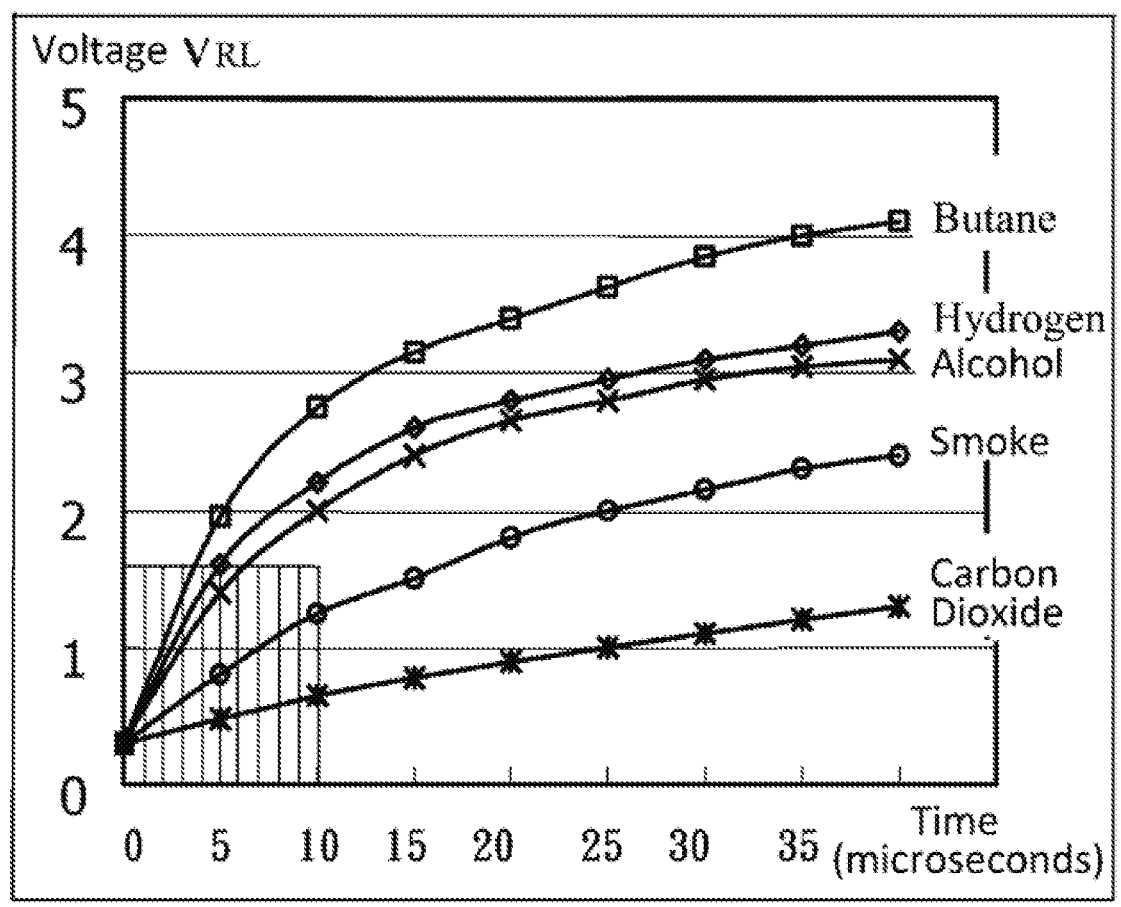
FIG. 2 is a curve diagram of a relationship between a voltage and a time of a gas detector according to a preferred embodiment of the present invention.

With reference to FIG. 2, a method of enhancing judgment of a gas detector according to a preferred embodiment of the present invention includes dividing a voltage difference between an output signal voltage and an environmental detection voltage of the gas detector into several parts (for example, the voltage difference is divided into 100 parts), wherein each of multiple detecting processes of the gas detector is captured by a microprocessor at the environmental detection voltage for ten times in each microsecond, and a predetermined detection time interval of each detecting process is 10 seconds, wherein when a relationship between a time of the environmental detection voltage and a voltage changes linearly (as shown in FIG. 2), the predetermined detection time interval of each detecting process is shortened to $1/10$ second. After three successive detection processes change linearly, a warning device is started (wherein the gas detector is configured to detect harmful gas and to produce a change of an electric signal). Otherwise, the gas detector determines that there is a natural change in an environment when temperature and humidity change (i.e., a non-linear change). In the meantime, the microprocessor compensates the output signal voltage and recovers the predetermined detection time when the environmental detection voltage changes so as to maintain the voltage difference at a certain value (for example, the environmental detection voltage is less than 0.5 volts of the output signal voltage, wherein when the microprocessor determines that the environmental detection voltage produces a 0.1 volt change with a change of temperature and humidity, the microprocessor requires the output signal voltage to produce the 0.1 volt change so that the environmental detection voltage is less than 0.5 volts of the output signal voltage, so as to avoid an error report because the environmental detection voltage has increased because of the temperature and humidity change). Preferably, a temperature sensor and a humidity sensor are not required because the microprocessor compensates the environmental detection voltage so as to respond the temperature and humidity change.

While various embodiments in accordance with the present invention have been shown and described, it is clear to those skilled in the art that further embodiments may be made without departing from the scope of the present invention.

What is claimed is:

1. A method of enhancing judgment of a gas detector comprising:

dividing a voltage difference between an output signal voltage and an environmental detection voltage of the gas detector into several parts, wherein each of multiple detecting processes of the gas detector is captured by a microprocessor at an environmental detection voltage ten times in each microsecond, and a predetermined detection time interval of each detecting process is 10 seconds, wherein when a determination is made that the environmental detection voltage has changed linearly, the predetermined detection time interval of each detecting process is shortened to $1/10$ second, and the multiple detecting processes of the gas detector continue to be captured by the microprocessor at the environmental detection voltage for ten times in each microsecond at the shortened detection time interval of each detection process of $1/10$ second, and after a determination is made that three successive detection processes have changed linearly, a warning device is started, otherwise, the microprocessor compensates the output signal voltage and recovers the predetermined detection time interval when the environmental detection voltage changes to maintain the voltage difference at a certain value.

2. The method as claimed in claim 1, wherein the voltage difference is divided into 100 parts.

* * * * *